USOO5763431A

United States Patent [19]

Jackson

[11] Patent Number: 5,763,431
[45] Date of Patent: Jun. 9, 1998

[54] METHOD FOR REGULATING NEUROPEPTIDE HORMONE SECRETION

[76] Inventor: Meyer B. Jackson, 3568 Tallyho La., Madison, Wis. 53705

[21] Appl. No.: 701,869

[22] Filed: Aug. 23, 1996

Related U.S. Application Data

[63] Continuation-in-part of Ser. No. 415,741, Apr. 3, 1995, Pat. No. 5,550,120, and a continuation of Ser. No. 109,683, Aug. 20, 1993, abandoned.

[51] Int. Cl.$^6$ .................. A61K 31/56; A01N 45/00
[52] U.S. Cl. .................. 514/169; 514/170; 514/177; 514/178
[58] Field of Search .................. 514/169, 170, 514/177, 178

[56] References Cited

U.S. PATENT DOCUMENTS 5,110,810  5/1992  Eich et al. .
5,120,723  6/1992  Gee et al. .

OTHER PUBLICATIONS

P. Johnson, *Drugs*, 45:684–692 (1993).
Van den Veyver et al., *Obstet. Gynecol. Survey*, 48:493–500 (1992).
B.M. Sibai, *Obstet Gynecol. Clinics.*, 19:615–632 (1992).
S.M. Paul et al., *FASEB J.*, 6:2311–2322 (1992).
M.D. Majewska, *Prog. Neurobiol.*, 38:379–395 (1992).
H.O. Garland et al., *J. Endocrinology*, 113:435–444 (1987).
S.J. Zhang et al., *Science*, 259:531–534 (1993).
E. Saridaki et al., *J. Endocrinol.*, 121:343–349 (1988).
R.M. Buijs, *Neurosci.*,20:347–355 (1987).
M. Molzbauer, *Med. Biol.*, 54:227–242 (1976).

*Primary Examiner*—Leon B. Lankford, Jr.
*Attorney, Agent, or Firm*—Teresa J. Welch; Stroud, Stroud, Willink, Thompson & Howard

[57] ABSTRACT

Methods are described for regulating neuropeptide secretion to alleviate premature labor, hypertension, fluid imbalance, and risk of heart disease using neuroactive steroids targeted for a newly-identified site of action in the nerve terminals of neurosecretory neurons.

10 Claims, 4 Drawing Sheets

CONTROL (GABA)

ALPHAXALONE + GABA

CONTROL (GABA)

ALLOPREGNANOLONE + GABA

CONTROL (GABA)

ESTRADIOL + GABA 50 pA
1 sec

METHOD FOR REGULATING NEUROPEPTIDE HORMONE SECRETION

This is a continuation-in-part of application Ser. No. 08/415,741 filed Apr. 3, 1995, now U.S. Pat. No. 5,550,120 which is a continuation of application Ser. No. 08/109,683, now abandoned.

TECHNICAL FIELD

The present invention is directed to a method for regulating the secretion of neuropeptide hormones. More specifically, the invention is to a method of using neuroactive steroids to regulate the secretion of neuropeptide hormones from nerve terminals having GABA receptors.

REFERENCES

The following references are cited throughout the text of this patent and are provided as background information to show the state of the art only. The citation of these references is not to be construed as an admission that they constitute prior art.

U.S. Patent Documents

| | | |
|---|---|---|
| 5,120,723 | 6/1992 | Gee and Bolger |

Other Publications

National Commission to Prevent Infant Mortality (1988).
Johnson, P. Drugs 45: 684–692 (1993).
Van den Veyver and Moise, K. J. Obstet. Gynecol. Survey 48:493–500 (1992).
Sibai, B. M. Obstet. Gynecol. Clinics. 19:615–632 (1992).
Haslam, R. J. & Rosson, G. M. Am. J. Physiol. 223:958–967 (1972).
Paul, S. M. & Purdy, R. H. FASEB J. 6:2311–2322 (1992).
Majewska, M. D. Prog. Neurobiol. 38:379–395 (1992).
Garland, H. O., Atherton, J. C., Baylis, C., Morgan, M. R. A. & Milne, C. M. J. Endocrinology 113:435–444 (1987).
Karavolas, H. J. & Hodges, D. R. Ciba Found. Symp. 153:22–55 (1990).
Zhang, S. J. & Jackson, M. B. (1993) Science 259, 531–534.
Saridaki, E., Carter, D. A. & Lightman, S. L. J. Endocrinol. 121:343–349 (1988).
Buijs, R. M., Van-Vulpen, E. H. S. & Geffard, M. (1987) Neurosci. 20, 347–355.
Raff, H. (1993). Interactions between neurohypophysial hormones and the ACTH-adrenocortical axis. Ann. NY Acad. Sci. 689, 411.
Rowland, M. In: *Clinical Pharmacology Basic Principles in Therapeutics* (Eds. K. L. Melmon and H. F. Morrelli) Macmillin Co., New York (1 972).
Goodman, A. G., Goodman, L. S., and Gilman, A. *Goodman and Gilman's the Pharmacological Basis of Therapeutics* Macmillan Co., New York (1980).

BACKGROUND OF THE INVENTION

Many hormones are secreted by neural processes emanating from the brain. Neurons have cell bodies at which electrical excitability is generated. After generation within the cell bodies, electrical impulses are propagated considerable distances along slender extensions called axons. Axons terminate in extensive terminal structures that contain specially packaged chemical substances. The arrival of electrical impulses into nerve terminals triggers the release of the chemical substances. Neurosecretory neurons are a special class of neurons that contain peptide hormones within their terminals and release these hormones into the blood. These hormones then circulate throughout the body and exert a wide variety of effects.

The neurohypophysis (posterior pituitary) consists of nerve terminals that secrete two peptide hormones. One of these hormones, oxytocin, stimulates uterine contractions during childbirth, lactation, and a variety of behavioral responses associated with reproduction. The other hormone, vasopressin (also known as antidiuretic hormone or ADH) stimulates water reabsorption by the kidney, blood pressure increases, and coagulation of blood through platelet aggregation. Controlling these functions can be of great value in medical situations, including conditions associated with or brought about by inappropriate, improperly regulated, or abnormal peptide hormone release. For example, premature labor is often associated with inappropriate oxytocin secretion. Swelling, edema, and bloating are often related to excessive vasopressin secretion. Risk of heart disease and heart conditions may also be increased by excessive vasopressin secretion.

Premature Labor

Premature delivery in pregnancy has been identified as the primary cause of increased infant mortality in the United States by the National Commission to Prevent Infant Mortality (1988). Between 5% and 9% of pregnancies result in premature delivery, and these premature births account for 60% of perinatal deaths. Surviving infants often suffer some form of handicap. The most widespread treatment of tocolysis has not reduced the frequency of premature births. At best tocolytic agents delay delivery by up to seven days and often bring on adverse side effects (Johnson, 1993). Prostaglandin synthase inhibitors have also been used to treat preterm labor. This treatment may be more effective in postponing parturition, but has serious fetal side effects (Van den Veyver and Moise, 1993). Improved treatment would be of great value in managing this medical problem.

Hypertension in Pregnancy

Between 5% and 10% of pregnancies are associated with some form of hypertensive disorder (Sibai, 1992). This includes a very broad class of disorders (e.g., preeclampsia) with symptoms including hypertension, edema, and proteinuria, which present at various times during or following pregnancy. These disorders are a major cause of both maternal and perinatal mortality. Many factors have been considered in the various hypertensive disorders associated with pregnancy. Treatment is varied and controversial.

Cardiovascular Disease and Reproductive State

Following menopause, the incidence of heart disease in women increases. Use of oral contraceptives also is associated with increased incidence of heart disease. In addition to taking a direct toll on health, the side effects of oral contraceptives have limited their widespread use. There is some evidence that vasopressin secretion is increased while a woman is on oral contraceptives. Such an increase may explain the link between oral contraceptives and heart disease. For example, hypercoagulability of blood is a major factor in the increased incidence of heart disease in both of these groups. Since vasopressin stimulates platelet aggregation (Haslam and Rosson, 1972), increases in vasopressin secretion could be responsible for the high risk of heart disease. What is needed is a way to control or reduce vasopressin secretion after menopause and during oral contraceptive use.

SUMMARY OF THE INVENTION

The above discussed problems associated with the presently available treatments for premature labor, hypertension and cardiovascular problems associated with oral contraception are alleviated by the methods of the present invention. The present invention is a method of regulating the levels of neuropeptide hormones in the blood of human patients, farm animals, and pets by using the class of compounds known to those skilled in the art as neuroactive steroids. This class of compounds acts at receptors for the inhibitory neurotransmitter GABA. GABA receptors reside in the membranes of the nerve terminals of neurosecretory neurons. The inventors' experiments have shown that these compounds can either enhance or reduce ongoing inhibition exerted by GABA. By acting on the membranes of neurosecretory nerve terminals, neuroactive steroids will reduce the secretion of neuropeptides. Reducing release of the neuropeptide oxytocin will be of value in controlling premature labor. Reducing the release of the neuropeptide vasopressin will be of value in controlling hypertension and cardiovascular problems. Methods are described for administering to human patients specific neuroactive steroids in pharmaceutically acceptable compositions, and thereby enhancing or depressing the release of peptide hormones from neurosecretory endings. Specifically, methods are described for administering neuroactive steroids to human patients suffering from or at risk for premature labor, hypertension, or cardiovascular disease.

DETAILED DESCRIPTION

Figure 1:
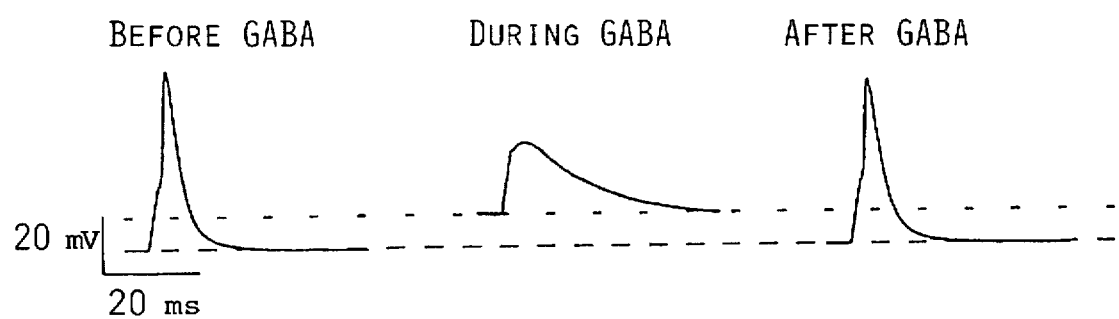
FIG. 1 is a terminal membrane action potential before and after GABA application.
Figure 2A:
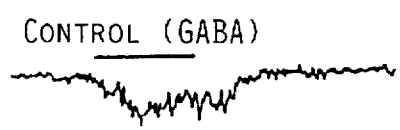
FIGS. 2A to 2C are whole-terminal patch clamp recordings showing the modulation of GABA responses by neuroactive steroids (Holding potential=−70 mV). 2A illustrates the effect of the mixture of GABA and alphaxalone compared to comtrol; 2B illustrates the mixture of GABA and allopregnanolone compared to control; 2C illustrates the application of GABA with estradiol-17b compared to control.
Figure 2A:
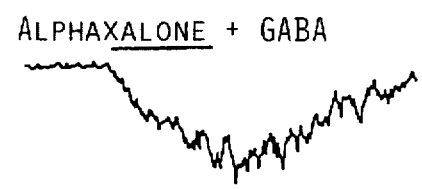
Figure 2B:
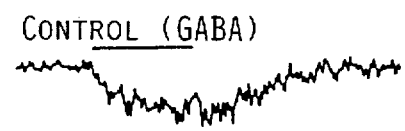
Figure 2B:
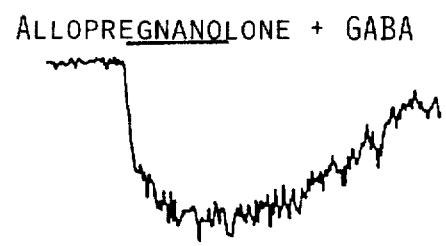
Figure 2C:
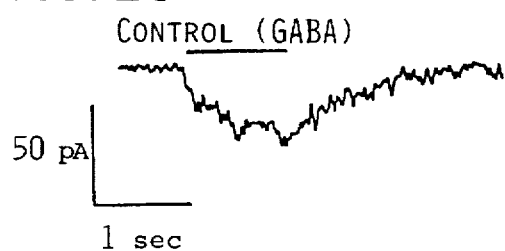
Figure 2C:
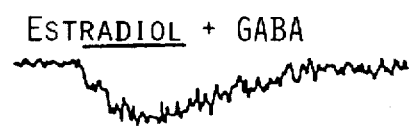

The compounds covered in this invention are various ester, oxime, and thiazolidine derivatives of 3-hydroxylated-5-reduced-20-ones, 5-reduced-3,21 -pregnanediol-20-ones, and 5-reduced-3,20-pregnandiols having substituent in the 9-position, which derivatives are referred to as prodrugs by those skilled in the art of pharmaceutical preparations, incorporated herein by reference. The compounds claimed in the present invention and methods for their preparation have been described in detail in patent of Gee and Bolger, U.S. Pat. No. 5,120,723, which is incorporated herein by reference. Among the compounds described in Gee, the preferred compounds for enhancing the inhibitory effect of GABA at the neurosecretory nerve terminal are epiallopregnanolone; pregnandiol; alphaxalone; 5α-androstan-3α, 17β-diol; 5α-pregnan-3α,21-diol-11,20-dione; 5α-androstan-17β-DL-3-one; allopregnanolone; pregnenolone; dehydroepiandrosterone; allotetrahydrodeoxycorticosterone; tetrahydrodeoxycorticosterone; 5α-pregnan-3α-ol-20-one; 5β-pregnan-3α-ol-20-one; 5α-pregnan-3α-21 diol-20-one; alfadolone; androsterone; pregnanolone; ganaxolone; and their physiological esters and salts.

The preferred compounds for reducing the inhibitory effect of GABA at neurosecretory nerve terminal are 17β-estradiol, estrone and and estradiol, and its sulfated derivative, the sulfated derivative of dehydoepiandrosterone (DHEA), a metabolic intermediate in the pathway for the synthesis of testosterone, DHEAS, pregnenolone sulfate.

Many of these compounds are natural products present in physiologically active concentrations in humans and experimental animals. The term "neuroactive steroids" includes substances such as the natural product allopregnanolone (3α-hydroxy-5α-pregnan-20-one; also known as 3α, 5α tetrahydroprogesterone) and the anesthetic alphaxalone. This group of 3-hydroxylated-5-reduced steroid derivatives has been previously shown to act at the cell bodies of neurons to modulate excitability (Paul and Purdy, 1992; Majewska, 1992).

The pharmaceutical compositions of this invention are prepared in conventional dosage unit forms by incorporating an active compound of the invention or a mixture of such compounds with a nontoxic pharmaceutical carrier according to accepted procedures in a nontoxic amount sufficient to product the desired pharmacodynamic activity in a subject, animal or human. Preferably, the composition contains the active ingredient in an active, but nontoxic amount, selected from about 50 mg to about 500 mg of active ingredient per dosage unit. This quantity depends on the specific biological activity desired and the condition of the patient. The most desirable object of the compositions and methods is in the treatment of premature labor, hypertension and heart disease.

The pharmaceutical carrier employed may be, for example, either a solid, liquid, or time release (see e.g., Remington's Pharmaceutical Sciences, 14th Edition 1970). Representative solid carriers are lactose, terra alba, sucrose, talc, gelatin, agar, pectin, acacia, magnesium stearate, stearic acid, microcrystalline cellulose, polymer hydrogels and the like. Typical liquid carriers are syrup, peanut oil, and olive oil and the like emulsions. Similarly, the carrier or diluent may include any time-delay material well known to the art, such glyceryl monostearate or glyceryl disterate alone or with a wax, microcapsules, microspheres, liposomes, and hydrogels.

A wide variety of pharmaceutical forms can be employed. Thus, when using a solid carrier, the preparation can be tableted, placed in a hard gelatin capsule in powder or pellet form, or in the form of a troche, lozenge, or suppository. When using a liquid carrier, the preparation can be in the form of a liquid, such as an ampule, or as an aqueous or nonaqueous liquid suspension. Liquid dosage forms also need pharmaceutically acceptable preservatives and the like. In addition, because of the low doses that will be required as based on the in vitro data disclosed herein, timed release skin patches are also a suitable pharmaceutical form for topical administration.

The amount of the compounds, either singly or mixtures thereof, of the invention administered at a dose which will generally achieve a physiological concentration and may be at the high or low physiological range depending on the effect that is desired. For example, if the desire is to suppress the release of oxytocin or vasopressin, allepregnanolone, or a progesterone metabolite similar to allepregnanolone may be administered at a dose to achieve a concentration which is at the high end of the physiological concentration range for such metabolites. The physiological range for such compounds is well known in the art.

The route of administration may be any route that effectively transports the active compound to the GABA receptors of the neurosecretory nerve terminals that are to be affected. Administration may be carried out parenterally, rectally, intravaginally, intradermally, sublingually, nasally or transdermally.

Knowledge of how to control the secretion of peptide hormones from nerve terminals is very limited because prior to research by the inventor, direct investigation of nerve terminal membranes was extremely difficult. The discovery by the inventor that neuroactive steroids can modulate membrane activity in the nerve terminals of the posterior pituitary thus provides a strategy for pharmacological intervention to control the release of peptide hormones from the nerve terminals of neurosecretory neurons.

$GABA_A$ receptors have been found in the nerve terminals of the posterior pituitary (Zhang and Jackson, 1993). However, in contrast to cell bodies where GABA increases chloride entry, in nerve terminals GABA increases chloride outflow (FIG. 1). Under most conditions a nerve cell has an interior that is more negative than the exterior, and this voltage difference is essential for impulse propagation. Chloride outflow initiated by GABA in nerve terminals makes the interior of the nerve terminal less negative than normal. Because a nerve membrane must have a negative potential difference of a minimum magnitude to support the propagation of electrical impulses, the loss of negative voltage halts impulse propagation. The block of propagation prevents the impulse from reaching nerve terminals, thus reducing the secretion of peptide hormones. Because of this novel mechanism by which GABA acts on nerve terminals, it was critical to test whether neuroactive steroids have an effect on the nerve terminal GABA receptor. By enhancing this action of GABA, neuroactive steroids act as useful therapeutic agents in controlling secretion of peptide hormones.

Data presented here shows the results of experiments with neuroactive steroids on $GABA_A$ receptor-mediated responses in posterior pituitary nerve terminals. In common with $GABA_A$ receptors in cell bodies, the nerve terminal receptor was potentiated by the synthetic steroid alphaxalone and the progesterone metabolite allopregnanolone. Furthermore, estradiol-17β had a weak inhibitory effect on GABA responses of nerve terminals. During pregnancy, high concentrations of circulating allopregnanolone would enhance GABAergic inhibition of oxytocin secretion. This could function to maintain oxytocin at low levels required for normal continuation of pregnancy. Likewise, the decline of allopregnanolone at parturition would reduce GABA-mediated inhibition to permit release of oxytocin and vasopressin. These results demonstrate a direct action of steroids at the nerve terminal membrane in the neurohypophysis, and thus demonstrate that neuroactive steroids can act on nerve terminals to influence neurosecretion.

Circulating oxytocin and progesterone levels exhibit an approximately reciprocal relationship during pregnancy and parturition in mammals, and the coordinated variation of these two hormones is essential to the orchestration of these and other reproductive functions. For example, in rats ovarian progesterone secretion peaks at the sixteenth day of gestation, and then declines abruptly at the onset of parturition. In contrast, plasma concentrations of oxytocin are low during pregnancy and become elevated during parturition (Garland et al., 1987). A rise in oxytocin plays an important role in the initiation of human labor. The earliest ideas about hormonal interactions during parturition in mammals focused on changes in the ratio of circulating estrogen to progesterone at the end of pregnancy to trigger fetal expulsion together with the onset of maternal behavior. The parallel changes in estradiol-17β and oxytocin thus contrast strikingly with the reciprocal relation between progesterone and oxytocin. Estradiol-17β remains low during the first half of pregnancy, and rises abruptly near term. Like oxytocin, the other major neurohypophysial peptide, vasopressin, is secreted during parturition, and is essential for maintaining blood pressure during the hemorrhage associated with parturition in some mammals. Thus, vasopressin and oxytocin appear to be influenced by ovarian steroids in a similar manner. Despite the manifest coordination between ovarian steroids and neurohypophysial peptides, the mechanistic links were unknown prior to the present studies.

The past decade has witnessed the emergence of neurosteroids, a group of steroids with novel actions at the membranes of excitable cells (Paul and Purdy, 1992; Majewska, 1992). However, while these phenomena are well established experimentally, physiological roles for the membrane actions of steroids remain elusive. The best example of these types of actions is the modulation of $GABA_A$ receptors, which has been shown in many types of cell bodies. Among naturally occurring steroids, one of the most potent substances with this action is the progesterone derivative allopregnanolone (3α-hydroxy-5α-pregnan-20-one; also known as 3α, 5α tetrahydroprogesterone). Allopregnanolone markedly enhances responses to agonists at the $GABA_A$ receptor. Progesterone is converted to allopregnanolone in the brain as well as in the pituitary (Karavolas and Hodges, 1990). The plasma and brain levels of allopregnanolone for the most part parallel those of progesterone (Paul and Purdy, 1992). Highest allopregnanolone levels are observed during pregnancy, proestrus, and estrus in rats. In women, the plasma levels of both allopregnanolone and pregnanolone are also highly correlated with progesterone levels during the menstrual cycle and pregnancy.

The inventors have recently shown that nerve terminals of the posterior pituitary contain a $GABA_A$ receptor coupled to a chloride channel (Zhang and Jackson, 1993). This receptor possesses many of the properties attributed to $GABA_A$ receptors in nerve cell bodies. Activation of these receptors by GABA and GABA mimetics reduces stimulus-evoked neuropeptide release from both isolated neural lobe and neurosecretosomes (Saridaki et al., 1988). GABA-containing nerve terminals have been demonstrated in the posterior pituitary, where they form synapse-like contacts with the peptidergic axon terminals (Buijs et al., 1987). These $GABA_A$ receptors provide a missing link between circulating steroids and neurohypophysial peptides by allowing steroids to contribute to the regulation of peptide secretion. Neuroactive steroids thus provide a form of gain control over the GABAergic innervation of the posterior pituitary. In order to test this hypothesis, we investigated the effects of neuroactive steroids on $GABA_A$ receptors at posterior pituitary nerve terminals.

FIG. 2 shows that both allopregnanolone and alphaxalone strongly enhanced GABA-activated Cl⁻ current in the nerve terminals of the posterior pituitary. These two compounds enhanced responses in every nerve terminal exhibiting a GABA response; since 89% of the nerve terminals in this preparation are responsive to GABA (Zhang and Jackson, 1993), and since roughly half of the nerve terminals contain either oxytocin or vasopressin, this means that neurosteroids are capable of modulating the secretion of either of these two peptides. Application of a mixture of GABA (40 mM) and alphaxalone (5 mM) produced responses 2.55 times as large as the control response produced by 40 mM GABA alone in the same nerve terminal (geometric mean of 10 experiments). Allopregnanolone (100 nM) enhanced GABA responses by a factor of 1.92 (n=5), and this concentration is similar to that seen in the circulation of both rats and humans during pregnancy (Paul and Purdy, 1992). In contrast to the actions of allopregnanolone and alphaxalone, estradiol-17β (100 nM) produced a small reduction of GABA responses to 78% of controls (n=6).

Figure 3A:
FIGS. 3A and 3B are whole terminal recordings showing the GABA desensitizing effect of certain neuroactive steroids on the $GABA_A$ receptor. 3A illustrates the effect of Alphaxalone. 3B illustrates the effect of allopregnanolone.
Figure 3B:
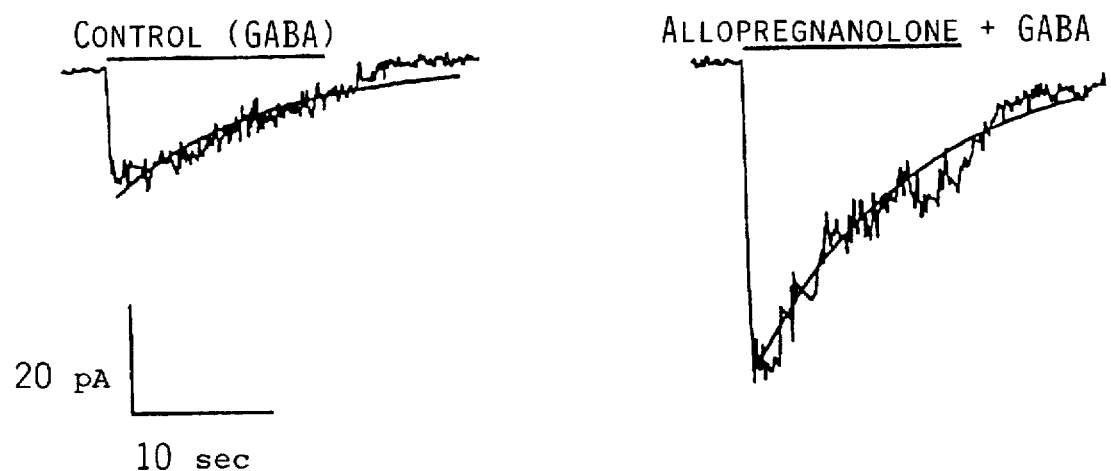

These same neuroactive steroids failed to alter the desensitization rate (FIG. 3). Sustained application of GABA desensitized the receptor with a time constant of 9.5±0.5 sec (n=3). In the presence of 5 mM alphaxalone desensitization had a very similar time constant of 8.9±0.5 sec (n=3) in the same terminals. Similar results were obtained with allopregnanolone; the average time constant for desensitization was 9.1±1.8 sec with GABA alone and 10.2±1.7 sec (n=3) with GABA and allopregnanolone. Estradiol-17β also failed to alter the rate of desensitization (9.2±0.2 sec for controls and 7.9±1.9 sec with estradiol-17β; n=2). Thus, the observed modulation does not result from an effect on agonist-induced desensitization.

Figure 4A:
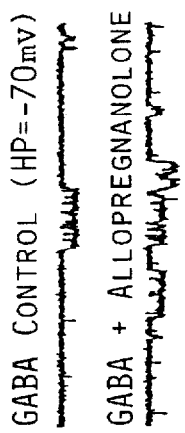
FIGS. 4A to 4D illustrates the effect of certain neuroactive steroids on $GABA_A$ receptor mediated $Cl^-$ single-channel currents recorded from outside-out patches excised from nerve terminals. 4A illustrates enhancement of GABA activated single-channel activity in outside-out patches by alphaxalone. 4B is an all-points amplitude distribution computed from 4A which shows that alphaxalone with GABA (filled circles) produced more channel activity than GABA alone (open circles). 4C illustrates enhancement of GABA activated single-channel activity by allopregnanolone. 4D is an all-points amplitude distribution computed from 4C which shows that allopregnanolone with GABA (filled circles) induced more channel activity than GABA alone (open circles).
Figure 4C:
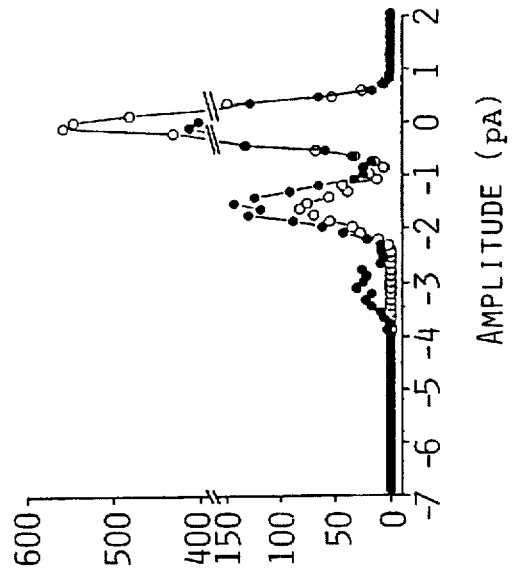
Figure 4B:
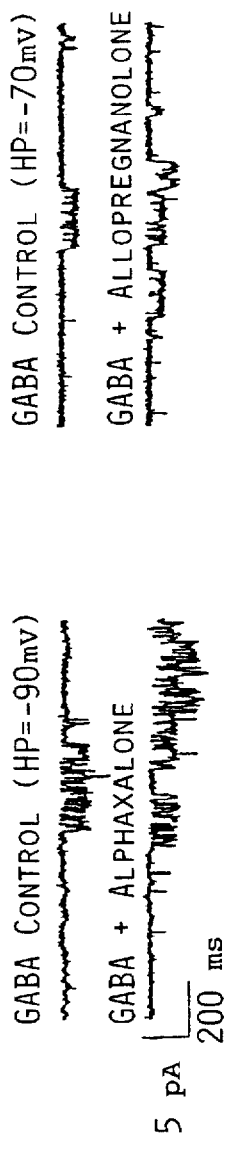
Figure 4D:
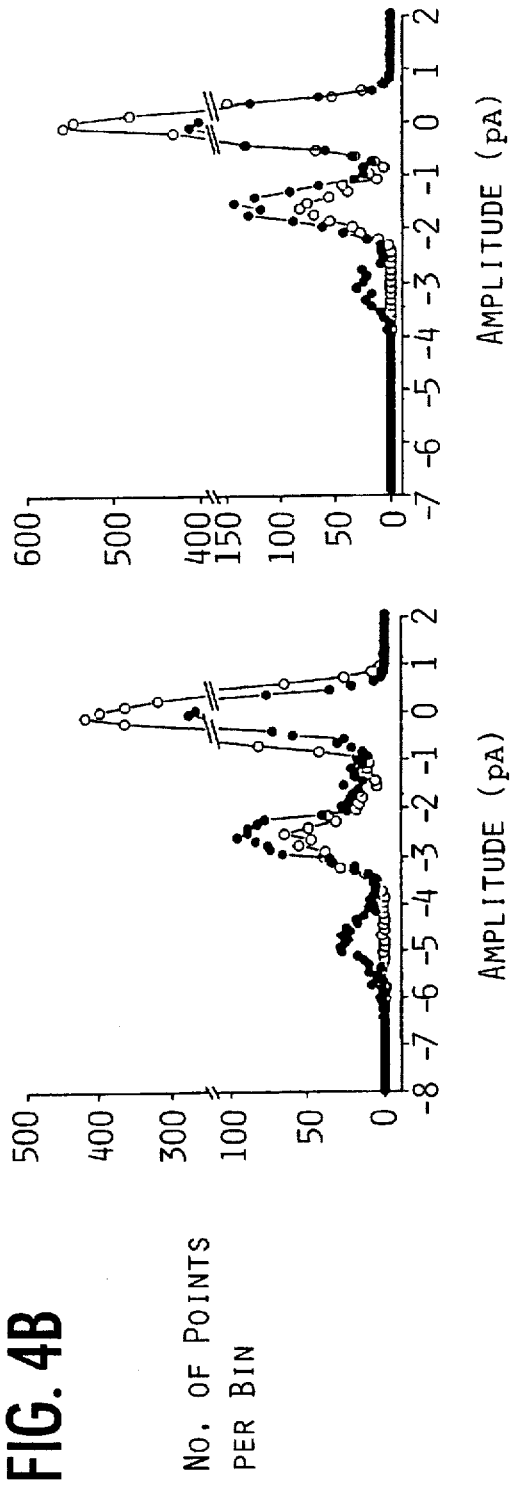

GABA-gated Cl⁻ single-channel currents (FIG. 4A and FIG. 4C) can be recorded from outside-out patches excised from posterior pituitary nerve terminals. In excised patches, neuroactive steroids displayed the same actions as in the whole-terminal recordings described above. In the presence of allopregnanolone or alphaxalone single channel activity clearly increased, while in the presence of estradiol-17b activity went down slightly. This can also be seen in amplitude distributions prepared from single-channel current recordings (FIGS. 4B and 4D). The greater area under the peaks representing one or more channel openings concomitant with a reduction in area of the peak representing times during which all channels are closed shows that channels spend more time in the open state when GABA is applied together with steroid. The identical spacing between these peaks in GABA alone or GABA+steroid indicates that the steroid has no effect on single channel conductance, but rather alters channel gating. The distributions in FIG. 4 can be used to compute a quantitative index of channel activity that compares well with steroid-induced changes in whole-terminal current (Table I). Thus, steroids modulate GABA responses by altering the open-closed conformational equilibrium of the GABA-ligated receptor. These experiments in excised-patches reaffirm the action of neurosteroids at the plasma membrane and are consistent with the presence of a binding site for steroids on the $GABA_A$ receptor protein.

These experiments showed that concentrations of allopregnanolone often found in the circulation of humans are sufficient to exert a physiological effect on the nerve terminals of neurosecretory neurons. This action prevents inappropriate oxytocin secretion during pregnancy. Should the posterior pituitary release oxytocin at some intermediate stage of pregnancy, premature labor and premature birth are likely to ensue. Administration of an effective amount of neuroactive steroid is therefore expected to forestall premature labor.

Table 1 summarizes the effects of steroids on the $GABA_A$ receptor of nerve terminals. Both alphaxalone and allopregnanolone strongly enhanced responses of the $GABA_A$ receptor by increasing channel open probability. Estradiol-17β had a weak inhibitory effect on the $GABA_A$ receptor. The actions in whole-terminal recordings and excised patches were generally consistent. Thus, neuroactive steroid antagonists as well as agonists are effective at the $GABA_A$ receptor in posterior pituitary nerve terminals. Neurosteroids that potentiate $GABA_A$ receptor mediated responses are well established, but neurosteroids with inhibitory actions have also been described (Paul and Purdy, 1992; Majewska, 1992). This would provide a means for bidirectional control over secretion from the posterior pituitary. In this way central GABAergic inputs to the posterior pituitary could be either enhanced or diminished.

By showing that a gonadal steroid derivative acts on receptors in the nerve terminals of the posterior pituitary, these experiments provided the first evidence for direct communication between the gonads and the neurohypophysis. The nature of this link fits very well with the concurrence of changes in circulating oxytocin and neuroactive steroids during the pregnancy-parturition transition and during the ovulatory cycles of mammals. This finding has important medical implications. First, premature labor is commonly associated with inappropriate oxytocin secretion. Some occurrences of premature labor are likely due to inappropriate reductions in circulating allopregnanolone. Second, the use of oral contraceptives is associated with high blood coagulability and a high incidence of heart disease. Oral contraceptives are generally mixtures of various steroids that could perturb balances between the many natural steroids, leading to excesses of vasopressin secretion. Since vasopressin stimulates platelet aggregation (Haslam and Rosson, 1972), this provides the link between oral contraceptives and heart disease. Third, alterations in fluid balance commonly accompany pregnancy and the luteal phase of the menstrual cycle, and this in part reflects direct steroid actions at the posterior pituitary. Finally, there is a high incidence of heart disease in women following menopause. After menopause the cyclic changes in progesterone, allopregnanolone and other steroids cease. This removes significant inhibitory factor to the release of vasopressin. With a decrease in such inhibitory factors, vasopressin secretion increases resulting in adverse cardiovascular effects.

Neuroactive steroids likely have a similar influence on the release of other peptide hormones in addition to oxytocin and vasopressin. GABA has been shown to inhibit release of other peptide hormones such as CRH and LHRH. The GABA receptors on the neurosecretory endings of these other peptidergic neurons are likely to resemble those in the posterior pituitary and thus respond to modulation by neuroactive steroids. The terminals of neurosecretory neurons could thus allow neuroactive steroids to play a role in many different endocrine functions, in addition to the already established role in mental functions (Paul and Purdy,1992; Majewska, 1992).

Since many of the target organs of the present invention, including the posterior pituitary, are outside the central nervous system, it may be desirable to modify the compounds of the present invention such that they will not pass the blood-brain barrier. The principle of blood-brain barrier permeability can therefore be used to design neuroactive steroid drugs with selective potency for peripheral targets. Such a drug will maintain effectiveness in enhancing or reducing neuropeptide release from the posterior pituitary, but will not produce the side effects often seen with neuroactive steroids such as sedation.

For example, the posterior pituitary lies outside the brain, so that drugs which are impermeable to the blood-brain barrier can reach this target to enhance or inhibit neuropeptide release without crossing the blood-brain barrier and causing unwanted side effects due to actions in the brain. The posterior pituitary is separated from the blood by a highly permeable capillary endothelium that allows free entry of large charged molecules which cannot permeate the blood-brain barrier.

In order for a drug to enter the brain and spinal cord and produce effects on the central nervous system, it must cross the blood-brain barrier. This generally requires some solubility of the drug in lipids. Conversely, a lipid-insoluble drug will not cross the blood-brain barrier, and will not produce effects on the central nervous system. Accordingly, it has been stated by Rowland (1972) "A basic drug that acts on the nervous system may be altered to produce a selective peripheral effect by quaternization of the drug, which decreases its lipid solubility and makes it virtually unavailable for transfer to the central nervous system." This principle has been used to develop drugs that act in peripheral tissues but spare the brain and spinal cord.

Two examples illustrate this principle. Among drugs that inhibit the enzyme acetylcholine esterase (anticholinesterases), the drugs neostigmine and edrophonium are charged and have only peripheral effects. These drugs can be used to treat heart conditions, paralytic ileus, and atony of the urinary bladder with minimal central effects. On the other hand, the anticholinesterase drug physostigmine carries no electrical charge and readily crosses the blood-brain barrier. Physostigmine can therefore be used to treat atropine poisoning and central anticholinergic syndrome. Another example can be found among drugs that act at muscarinic acetylcholine receptors. The charged antimuscarinic drug methscopalamine bromide can thus be used to treat gastrointestinal diseases and the uncharged antimuscarinic drug scopolamine can be used to treat motion sickness.

Applying similar principals to the neuroactive steroids of the present invention, one can modify such compounds using well known standard chemical synthetic techniques to add a lipid impermeable functional group such a quaternary amine, sulfate, carboxylate, phosphate, or sulfonium. Examination of the activity of steroid analogs has shown that an a hydroxyl at the 3 position (R1) is essential for enhancing activity at the $GABA_A$ receptor, while a sulfate at the 3 position confers antagonist activity at the $GABA_A$ receptor. Structural variations at other locations seem to have little if any effect on biological potency. Thus, alfaxalone, allopregnanolone, allotetrahydrodeoxycorticosterone, and dehydroepiandrosterone, all potent neuroactive steroids, have different substituents at R2 and R3 of the basic steroid structural backbone (as illustrated in Formula I), but maintain strong activity in enhancing $GABA_A$ receptors. Sites such as these provide opportunities to modify the basic structure in order to create drugs with special properties. In the preferred embodiment of the present invention, therefore, the desired neuroactive steroid is modified by adding at R2 or R3, or at R4, R5, or R6, of the basic steroid structural backbone illustrated in Formula I a quaternary amine, sulfate, carboxylate, phosphate or sulfonium group. Such a modification maintains the biological potency of the molecule but makes it impermeable to the blood-brain barrier. Such modification is by no means the only way in which the neuroactive steroids of the present invention may be modified to be impermeable to the blood-brain barrier; other well known pharmaceutical techniques exist and would be considered to fall within the scope of the present invention.

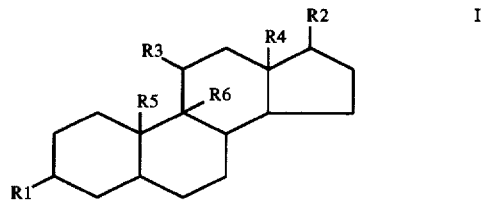

EXAMPLE 2

Treatment and Prevention of Hypertension

An experiment is run with study group of patients who are borderline hypertensive. Half of the group is given daily a high physiological dosage of allepregnanolone. The remaining patients are placed on placebo. After one year, the experimental group is expected to demonstrate a significantly lower blood pressure relative to control.

EXAMPLE 3

Oral Contraceptive Containing Neuroactive Steroid

An experiment is run with a study group of premenopausal women. Half of the group is placed on a progesterone containing oral contraceptive which also contains a neuroactive steroid such as allepregnanolone. The other half of the study group is given the same oral contraceptive but without neuroactive steroid. The study is run for two years and the group is regularly evaluated for its cardiovascular status. At the end of two years the group receiving neuroactive steroid is expected to demonstrate a significantly better cardiovascular status compared to control.

EXAMPLE 4

Use of Neuroactive Steroid to Induce Natural Labor

The neurosteroid antagonists of the present invention may be used to enhance release of oxytocin in the induction of active labor, the enhancement of uterine contractions during labor, and promoting uterine contractions after delivery of the placenta.

Physicians make a decision to induce labor when there is maternal illness, fetal distress, or, more commonly, prolonged pregnancy. Oxytocin (Pitocin) is routinely administered to induce active labor, to stimulate weak contractions in labor, and to cause contraction of the uterus after delivery of the placenta. Other agents used to induce labor include prostaglandins and progesterone antagonists. Induction of labor can result in uterine hyperstimulation, and poor neonatal outcome. To minimize these outcomes, a labor induction protocol should strive to mimic the normal physiological progression of parturition, but this is difficult with existing methods.

Oxytocin administration causes a steady sustained increase in the circulating level of the hormone. During normal parturition secretion of oxytocin by the posterior pituitary is pulsatile; release occurs at well separated intervals varying from five to ten or more minutes. Elaborate efforts have been made to mimic this process by administering oxytocin in larger doses at well-timed intervals. A neurosteroid antagonist has a specific mode of action that will enhance oxytocin release by increasing the release elicited by the naturally occurring pulsatile electrical activity in the posterior pituitary. Thus, a neurosteroid will enhance oxytocin release while maintaining the natural pulsatility, and this should provide a more natural method of inducing labor, enhancing contractions, and inducing uterine contractions after delivery of the placenta.

An experiment is run with a study group of pregnant women who required induction of labor. Half of the group is given Pitocin and the other half is given a medicament containing pregnenolone sulfate, a neurosteroid antagonist. The group given the pregnenolone sulfate formulation show enhanced contractions with a natural pulsatility.

EXAMPLE 5

Use of Neuroactive Steroids to Inhibit ADH Release in the Treatment of SIADH

In the fields of renal physiology and fluid balance the pituitary hormone vasopressin is often referred to as ADH. SIADH is a well known clinical condition caused by excessive secretion of ADH. In some cases ADH is secreted from ectopic tumors, and since in these cases the source of the ADH is not nerve terminals, these cases do not fall under the claim. However, many cases of SIADH do not arise from ectopic tumors, and in these cases the source of the ADH is the posterior pituitary. This syndrome can arise during a variety of conditions including cancer and cardiac failure. SIADH is also a frequent side effect of many drugs.

Hyponatremia and hypokalemia often present under the same conditions as SIADH. The excessive ADH secretion leads to excessive renal water retention by the kidneys. As a result of excessive renal water retention blood sodium and potassium is diluted leading to hyponatremia and hypokalemia, respectively.

EXAMPLE 6

Use of Neuroactive Steroids to Inhibit ADH Release in Adrenal Crisis

Steroids (e.g., prednisone) are administered during rheumetalogic, pulmonary, and inflammatory conditions, as well as during organ transplantation or situations requiring suppression of the immune system. When this steroid treatment is chronic, it alters the normal feedback mechanisms that regulate adrenal output of corticosteroids. When a patient is subsequently traumatized (for example by surgery), or if treatment stops abruptly, normal physiological demands for corticosteroids are not met. This brings on a condition of adrenal crisis with symptoms including hyponatremia, hyperkalemia, SIADH, and hemodynamic instability, leading to profound hypotension and cardiovascular collapse. It has been pointed out (Raff, 1993) that changes in mineralcorticosteroid (aldosterone) production cannot account for all of the fluid imbalance associated with many such instances of adrenal crisis. A plausible explanation can be offered for some of the fluid balance symptoms of adrenal crisis based on the discovery of the inventor that neurosteroids can modulate secretion of ADH from the posterior pituitary. The neurosteroid allotetrahydrodeoxycorticosterone is derived from the corticosteroid deoxycorticosterone. Thus, the adrenal gland can regulate ADH secretion by altering circulating levels of this neurosteroid. Failure of the body to produce allotetrahydrodeoxycorticosterone could then play an important role in adrenal crisis. This suggests that neurosteroid agonists could be used in treatment and/or prevention of adrenal crisis.

EXAMPLE 7

Use of Neuroactive Steroids to Suppress Lactation in Women

It is well known that oxytocin mediates the milk letting down reflex. A neurosteroid agonist will increase the inhibitory effect of the GABA receptor and thus decrease the amount of oxytocin released. By administering a physiological amount of a neurosteroid agonist such as allopregnanolone, it is expected that the lactation in nursing mothers would be suppressed.

EXAMPLE 8

Use of Neuroactive Steroids to Prevent Interruption of Parturition in Farm Animals Stress can interrupt parturition, and this can be a problem in the management of reproduction of farm animals. The stress response involves release of corticosteroids, and a derivative of deoxycorticosterone, allotetrahydrodeoxycorticosterone, is a potent neuroactive steroid that, based on the inventors discovery, can be expected to inhibit oxytocin release from the posterior pituitary. To the extent that oxytocin plays a role in parturition, a direct link between stress and parturition can be established. A neurosteroid antagonist would then be a natural method to overcome the disruption of parturition.

EXAMPLE 9

Use of Neuroactive Steroids to Increase Milk Production in Farm Animals

Oxytocin mediates the milk letting down reflex to eject milk from the udder. Stimulation of the teat either by suckling or other mechanical stimulation elicits a neural response in the hypothalamus after several minutes. The hypothalamic response consists of an intense surge of electrical activity in oxytocin cells. The nerve terminals of these cells in the posterior pituitary then release a large amount of oxytocin which circulates to the udder to induce the release of milk. A neurosteroid antagonist will enhance oxytocin secretion and thus produce a stronger milk letting down reflex. This should enhance milk output from farm animals. The time required to initiate the milk letting down reflex will then be shortened, thus reducing the time necessary for udder stimulation. This shortening of time for milking may be advantageous in reducing mastitis and other complications associated with mechanical milking.

EXAMPLE 10

Use of Neuroactive Steroids to Treat Impotence in Humans

In addition to the classical actions of oxytocin in stimulating uterine contractions and lactation, oxytocin has recently been found to play a role in sexual arousal. Oxytocin levels rise during sexual activity, and oxytocin injections can induce penile erection in experimental animals. Oxytocin also increases the motility of the vas deferens to promote sperm ejection. A neurosteroid antagonist will therefore enhance oxytocin secretion and thus enhance sexual function.

While the preferred embodiments have been described and illustrated, various substitutions and modifications may be made thereto without departing from the scope of the invention. Accordingly, it is to be understood that the present invention has been described by way of illustration and not limitation.

TABLE I

Steroid Actions at the Posterior Pituitary $GABA_A$ Receptor

| Steroid | Whole-Terminal Response Amplitude Ratio | Desensitization Time-Constant Ratio | Single-Channel Activity Ratio |
|---|---|---|---|
| Alphaxalone (5 mM) | 2.55 (n = 1.0)* | 1.06 (n = 3) | 1.76 (n = 4)* |
| Allopregnanolone (100 nM) | 1.92 (n = 5)* | 1.14 (n = 3) | 2.08 (n = 4)* |
| Estradiol-17β (100 nM) | 0.78 (n = 6)* | 0.90 (n = 2) | 0.74 (n = 4)* |

Measurements were made in nerve terminals for responses to GABA alone or GABA+steroid. The ratios were computed as (GABA+steroid)/GABA, and the geometric means were computed for the indicated number of ratios. The * indicates statistical significance at the level of P<0.05. Note that because these values are geometric means, they do not agree precisely with the ratios computed from arithmetic means of time constants given in text. The response amplitude ratio was computed from the peak whole-terminal responses such as shown in FIG. 2. The desensitization time constants were determined from single exponential fits as shown in FIG. 3. The single-channel activity was determined from $P_o$ using all-points histograms such as those shown in FIGS. 4B and 4D, as described in METHODS. The GABA concentration was 40 mM for the first two columns and 1 mM for the last column.

I claim:

1. A method for depressing in a patient the release of neuropeptide hormones from peripheral neurosecretory nerve terminals responsive to the neurotransmitter GABA without directly altering the activity of similarly responsive nerve cells of the patient's central nervous system, said method comprising the steps of:

(a) selecting a neuroactive steroid having an alpha-hydroxyl group at the 3 position of the neuroactive steroid molecule;

(b) modifying said neuroactive steroid so as to be impermeable to the blood-brain barrier by adding a charged group at a position on said neuroactive steroid molecule other than the 3 position;

(c) administering to said patient said modified neuroactive steroid in an amount sufficient to increase the inhibitory effect of GABA at said peripheral neurosecretory nerve terminals and thereby depress the release of neuropeptide hormones from said peripheral nerve terminals without directly altering the activity of similarly responsive cells in said patient's central nervous system.

2. A method as claimed in claim 1, wherein said charged group is selected from the group consisting of quaternary amines or sulfoniums.

3. A method as claimed in claim 1, wherein said neuroactive steroid has the general formula:

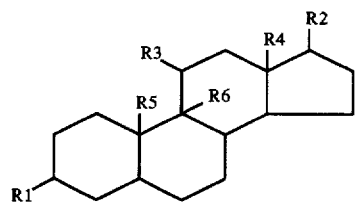

wherein

R1 is a alpha-hydroxyl,

R2 is selected from the group consisting of OH, acetyl, 2-hydroxyethanonyl, 1-hydroxyethyl,

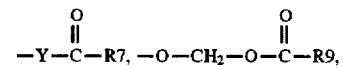

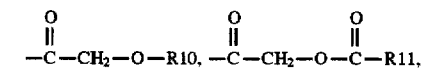

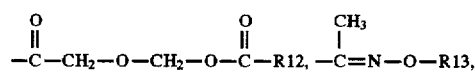

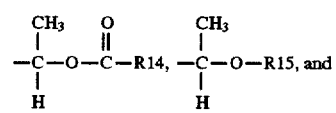

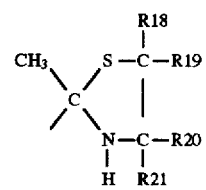

wherein

R7, R8, and R9 are individually a $C_1$–$C_{20}$ straight chain aliphatic radical, $C_1$–$C_{20}$ branched chain aliphatic radical, or $C_3$–$C_{10}$ cyclic aliphatic radical, or $C_3$–$C_{10}$ aromatic radical, or a heterocyclic radical selected from the group consisting of 1-methyl-1,4-dihydronicotinoyl, piperidinyl, pyridinyl, furanyl, thiphenyl, and pyrzinyl, and Y is —O— or —S—; and R10, R11, R12, R13, R14, R15, R18, R19, R20, and R21 are individually a $C_1$–$C_{20}$ straight chain aliphatic radical, $C_1$–$C_{20}$ branched chain aliphatic radical, or $C_3$–$C_{10}$ cyclic aliphatic radical or $C_3$–$C_{10}$ aromatic radical, or a heterocyclic radical selected from the group consisting of 1-methyl-1,4-dihydronicotinoyl, piperidinyl, pyridinyl, furanyl, thiophenyl, and pyrazinyl with the provisos that (1) R10, R11, and R12 may also individually be an amide

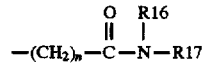

radical wherein

R16 and R17 individually are a $C_1$–$C_{20}$ straight chain aliphatic radical, $C_1$–$C_{20}$ branched chain aliphatic radical, or $C_3$–$C_{10}$ cyclic aliphatic radical, or $C_3$–$C_{10}$ aromatic radical, or a heterocyclic radical selected from the group consisting of 1-methyl-1,4-dihydronicotinoyl, piperidinyl, pyridinyl, furanyl, thiophenyl, and pyrazinyl, and n=1 to 8 and (2) R20 and R21 may also individually be H or

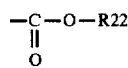

wherein

R22 is H or a $C_1$-$C_{20}$ straight chain aliphatic radical, $C_1$-$C_{20}$ branched chain aliphatic radical, or $C_3$-$C_{10}$ cyclic aliphatic radical, or $C_3$-$C_{10}$ aromatic radical, or a heterocyclic radical selected from the group consisting of 1-methyl-1,4-dihydronicotinoyl, piperidinyl, pyridinyl, furanyl, thiophenyl, and pyrazinyl, and n is an integer of 1 to 8;

R3 is selected from the group consisting of hydrogen, hydroxy, keto, $C_1$-$C_{18}$ alkyloxy, aryloxy, and amino; and R4, R5, and R6 individually are selected from the group consisting of $C_1$-$C_{18}$ alkyl, aryl, halo, and trifluoroalkyl.

4. A method as claimed in claim 3, wherein said charged group is added at position R2, R3, R4, R5, or R6 of said neuroactive steroid.

5. A method as claimed in claim 4, wherein said charged group is selected from the group consisting of quaternary amines or sulfoniums.

6. A method for enhancing in a patient the release of neuropeptide hormones from peripheral neurosecretory nerve terminals responsive to the neurotransmitter GABA without directly altering the activity of similarly responsive nerve cells of the patient's central nervous system, said method comprising the steps of:

(a) selecting a neuroactive steroid having a sulfate group at the 3 position of the neuroactive steroid molecule;

(b) modifying said neuroactive steroid so as to be impermeable to the blood-brain barrier by adding a charged group at a position on said neuroactive steroid molecule other than the 3 position;

(c) administering to said patient said modified neuroactive steroid in an amount sufficient to reduce the inhibitory effect of GABA at said peripheral neurosecretory nerve terminals and thereby enhance the release of neuropeptide hormones from said peripheral nerve terminals without directly altering the activity of similarly responsive cells in said patient's central nervous system.

7. A method as claimed in claim 6, wherein said charged group is selected from the group consisting of quaternary amines or sulfoniums.

8. A method as claimed in claim 6, wherein said neuroactive steroid has the general formula:

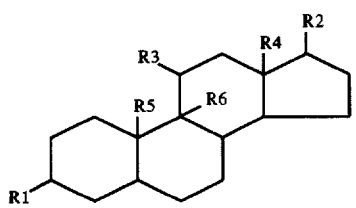

R1 is a sulfate group,

R2 is selected from the group consisting of OH, acetyl, 2-hydroxyethanonyl, 1-hydroxyethyl,

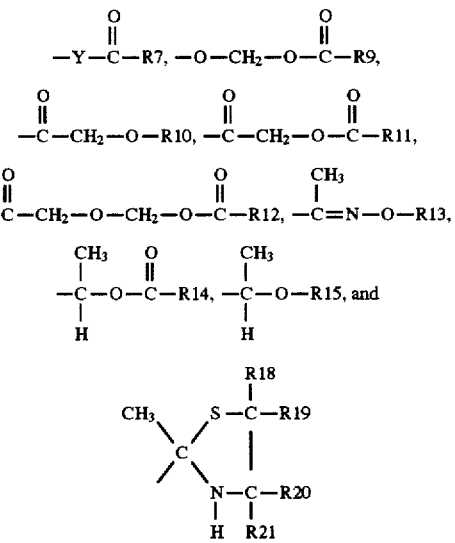

wherein

R7, R8, and R9 are individually a $C_1$-$C_{10}$ straight chain aliphatic radical, $C_1$-$C_{20}$ branched chain aliphatic radical, or $C_3$-$C_{10}$ cyclic aliphatic radical, or $C_3$-$C_{10}$ aromatic radical, or a heterocyclic radical selected from the group consisting of 1-methyl-1,4-dihydronicotinoyl, piperidinyl, pyridinyl, furanyl, thiphenyl, and pyrzinyl, and Y is —O— or —S—; and R10, R11, R12, R13, R14, R15, R18, R19, R20, and R21 are individually a $C_1$-$C_{20}$ straight chain aliphatic radical, $C_1$-$C_{20}$ branched chain aliphatic radical, or $C_3$-$C_{10}$ cyclic aliphatic radical or $C_3$-$C_{10}$ aromatic radical, or a heterocyclic radical selected from the group consisting of 1-methyl-1,4-dihydronicotinoyl, piperidinyl, pyridinyl, furanyl, thiophenyl, and pyrazinyl with the provisos that (1) R10, R11, and R12 may also individually be an amide

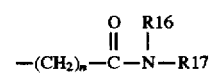

radical wherein

R16 and R17 individually are a $C_1$-$C_{20}$ straight chain aliphatic radical, $C_1$-$C_{20}$ branched chain aliphatic radical, or cyclic aliphatic radical, or $C_3$-$C_{10}$ aromatic radical, or a heterocyclic radical selected from the group consisting of 1-methyl-1,4-dihydronicotinoyl, piperidinyl, pyridinyl, furanyl, thiophenyl, and pyrazinyl, and n=1 to 8 and (2) R20 and R21 may also individually be H or

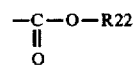

wherein

R22 is H or a $C_1$-$C_{20}$ straight chain aliphatic radical, $C_1$-$C_{20}$ branched chain aliphatic radical, or $C_3$-$C_{10}$ cyclic aliphatic radical, or $C_3$-$C_{10}$ aromatic radical, or a heterocyclic radical selected from the group consisting of 1-methyl-1,4-dihydronicotinoyl, piperidinyl, pyridinyl, furanyl, thiophenyl, and pyrazinyl, and n is an integer of 1 to 8;

R3 is selected from the group consisting of hydrogen, hydroxy, keto, $C_1$–$C_{18}$ alkyloxy, aryloxy, and amino; and R4, $R_5$, and R6 individually are selected from the group consisting of $C_1$–$C_{18}$ alkyl, aryl, halo, and trifluoroalkyl.

9. A method as claimed in claim 8, wherein said charged group is added at position R2, R3, R4, R5, or R6 of said neuroactive steroid.

10. A method as claimed in claim 9, wherein said charged group is selected from the group consisting of quaternary amines or sulfoniums.

* * * * *